(12) United States Patent
Danes et al.

(10) Patent No.: US 9,630,348 B2
(45) Date of Patent: Apr. 25, 2017

(54) DETECTION IN THERMOPLASTICS

(71) Applicants: Jeffrey E. Danes, San Luis Obispo, CA (US); Keith L. Vorst, Atascadero, CA (US)

(72) Inventors: Jeffrey E. Danes, San Luis Obispo, CA (US); Keith L. Vorst, Atascadero, CA (US)

(73) Assignee: Dialogr Systems, LLC, San Luis Obispo, CA (US)

( * ) Notice: Subject to any disclaimer, the term of this patent is extended or adjusted under 35 U.S.C. 154(b) by 410 days.

(21) Appl. No.: 13/893,305

(22) Filed: May 13, 2013

(65) Prior Publication Data
US 2014/0332994 A1   Nov. 13, 2014

(51) Int. Cl.
*B07C 5/00* (2006.01)
*B29B 17/00* (2006.01)

(52) U.S. Cl.
CPC .............. *B29B 17/00* (2013.01); *Y02W 30/62* (2015.05)

(58) Field of Classification Search
CPC ........ B29C 17/00; Y02W 30/62; G01N 21/25
See application file for complete search history.

(56) References Cited

U.S. PATENT DOCUMENTS

| | | | |
|---|---|---|---|
| 5,424,013 A | 6/1995 | Lieberman | |
| 5,567,623 A | 10/1996 | Rounbehler | |
| 6,099,659 A | 8/2000 | Tacito | |
| 6,533,124 B1 | 3/2003 | Tacito et al. | |
| 8,063,374 B2 * | 11/2011 | Vorst et al. | 250/339.08 |
| 2004/0149911 A1* | 8/2004 | Irie | G01N 21/3563 |
| | | | 250/339.12 |
| 2006/0017914 A1* | 1/2006 | Riess et al. | 356/51 |
| 2010/0256290 A1 | 10/2010 | Costanzo | |
| 2011/0068262 A1 | 3/2011 | Vorst | |
| 2011/0209715 A1 | 9/2011 | Burdumy | |
| 2012/0296572 A1 | 11/2012 | Hess et al. | |
| 2014/0278142 A1 | 9/2014 | Danes | |

OTHER PUBLICATIONS

Ezrin, Myer and Gary Lavigne, "Gas Chromatography/Mass Spectroscopy for Plastics Failure Analysis", ANTEC, 2004, pp. 3000-3004.*
Nagel; "Plastic glut grows as China turns back dirty recyclables"; Maple Ridge News.com; http://www.mapleridgenews.com/news/205681501.html; published May 1, 2013; downloaded May 6, 2013.
Zhang et al.; Artificial neural networks applied to polymer composites: a review; Composites Science and Technology; 2003; vol. 63, No. 14; pp. 2029-2044.

(Continued)

*Primary Examiner* — Galen Hauth
(74) *Attorney, Agent, or Firm* — Fitch, Even, Tabin & Flannery LLP

(57) ABSTRACT

A method including steps of providing at least one sensor; detecting a plurality of parameters in a thermoplastic using the at least one sensor; generating a plurality of outputs in response to the detecting; and characterizing a contaminant or a percentage of post-consumer recycled thermoplastic content in the thermoplastic as a function of the plurality of outputs having been generated and a thermoplastic pattern signature.

15 Claims, 14 Drawing Sheets

(56) References Cited

OTHER PUBLICATIONS

International Search Report and Written Opinion of the International Searching Authority for International Application No. PCT/US2014/037707 mailed on Sep. 1, 2014 (20059-130702-WO).
Curtzwiler et al.; "Effect of recycled poly(ethylene terephthalate) content on properties of extruded poly(ethylene terephthalate) sheets"; Journal of Plastic Film & Sheeting; vol. 27 (1-2); 2011; pp. 65-86.
Szczurek et al.; "Assessment of VOCs in air using sensor array under various exposure conditions"; IEEE; 2012; 5 pages.
Vorst et al.; "Keeping an Eye on Contamination: A Unique Process for Contamination Monitoring in Recovered Plastic Scrap Promises to Improve the Efficiency of Recycling Process. What are the Challenges Facing Increased RPET Use and How Do We Move Forward="; Plastics Recycling; Aug. 2012, pp. 20-23.
Bernardo et al.; "The Recycling of Thermoplastics: Prediction of the Properties of Mixtures of Virgin and Reprocessed Polyolefins"; Polymer Engineering and Science; Feb. 1996; vol. 36, No. 4; pp. 511-519.
Dutra et al.; "Determination of volatile organic compounds in recycled polyethylane terephthalate and high-density polyethylene by headspace solid phase microextraction gas chromatography mass spectrometry to evaluate the efficiency of recycling processes"; Journal of Chromatography A; vol. 1218; 2011; pp. 1319-1330.
Kanan et al.; "Semiconducting Metal Oxide Based Sensors for Selective Gas Pollutant Detection"; Sensors; published Oct. 16, 2009; pp. 8158-8196.
Kang et al.; "An exploratory model for predicting post-consumer recycled PET content in PET sheets"; Polymer Testing; vol. 30; Oct. 28, 2010; pp. 60-68.
Lee et al.; "Recognition of volatile organic compounds using SnO2 gas sensor array and pattern recognition analysis"; Sensors and Actuators; vol. B 77; 2001; pp. 228-236.
Lee et al.; "Fabrication and characteristics of SnO2 gas sensor array for volatile organic compounds recognition"; Thin Solid Films; vol. 416; Jun. 25, 2002; pp. 271-278.
Llobet et al.; "Qualitative and quantitative analysis of volatile organic compounds using transient and steady-state responses of a thick-film tin oxide gas sensor array"; Sensors and Actuators; vol. B 41; Jan. 29, 1997; pp. 13-21.
Nakano et al; "Preparation of calibrating standards for x-ray fluorescence spectrometry of trace metals in plastics"; X-Ray Spectrometry; vol. 32; May 19, 2003; pp. 452-457.
Schmitt; "New Method for Real-time Monitoring of Photopolymerization by UV-Vis Spectroscopya"; Macromolecular Chemistry and Physics; vol. 212; 2011; pp. 1276-1283.
Sarrabi et al.; "Real Time Analysis of Volatile Organic Compounds from Polypropylene Thermal Oxidation Using Chemical Ionization Fourier Transform Ion Cyclotron Resonance Mass Spectrometry"; Analytical Chemistry, vol. 81, No. 15; Aug. 1, 2009; pp. 6013-6020.

\* cited by examiner

DETECTION IN THERMOPLASTICS

BACKGROUND OF THE INVENTION

1. Field of the Invention

The present embodiments refer generally to systems and methods for thermoplastics contamination detection, and characterization, and more specifically to verification of contamination pattern signatures in virgin and post-consumer recycled thermoplastic materials. The embodiments also refer generally to systems and methods for the detection, characterization, and verification of a pattern signature reflecting the manufacturers intended percentage of post-consumer recycled thermoplastic material in the finished product (% PCR).

2. Discussion of the Related Art

Post-consumer recycled (PCR) plastic material is made by collecting used plastic products (e.g., bottles or other plastic packaging materials) and processing them into pellets or particles. Plastic recycling has positive environmental benefits (is "green") but also carries a downside in that recycled content made into products may contain unwanted organic and inorganic contaminants (is "unclean") that may leach into unwanted areas, such as into products contained within (packaged within packaging) containers (packaging) made from recycled plastic materials.

In 2012, more than 280 million tons of plastic were produced worldwide. Less than half has ended up in landfills or was recycled. Some of the unaccounted for 150 million tons litter cities, towns, open areas, and oceans. When thermoplastics break down in the environment they create toxic particles harmful to living things.

Globally there is mounting social and political pressure to increase recycling of thermoplastic materials. The National Association for PET Container Resources reports that 1.5 billion pounds of polyethylene terephthalate (PET) were recycled in 2010, and producing new products from recycled polyethylene terephthalate (RPET) uses two-thirds less energy than what is required to make products from raw virgin materials. Producing new products from recycled polyethylene terephthalate also reduces greenhouse gas emissions as compared to from virgin material.

The downside to recycling is post-consumer recycled materials may include metallic content and other contaminants (e.g., volatile organic compounds) that can leach out of extruded or molded materials into a product held within packaging. Leaching is a serious concern for plastics that are used to package and store, e.g., food and medical products (i.e., products that are ingested and/or injected into a living body, e.g., a human body).

Given the dangers associated with the leaching of chemicals and undesirable metallic content from plastic packaging into food and/or medical products, the Code of Federal Regulations (CFR), for example, limits the acceptable amount of such leaching. These limits vary depending on the nature of the compound containing, e.g., the food product. Moreover, it is difficult to know if the molding/extrusion of resultant materials yields a product that meets the Code of Federal Regulations requirement.

Many goods and services are promoted with claims of percentages of post-consumer recycled (% PCR) material used in packaging and other thermoplastic products. Manufacturers have begun to make broad marketing claims regarding percentages of post-consumer recycled thermoplastic material in their products and product packaging as consumers become aware of the impacts on environmental and personal health.

SUMMARY OF THE INVENTION

The present invention, in accordance with one embodiment can be characterized as a method including steps of providing at least one sensor; detecting a plurality of parameters in a thermoplastic using the at least one sensor; generating a plurality of outputs in response to the detecting; and characterizing a contaminant (organic or inorganic) in the thermoplastic as a function of the plurality of outputs having been generated and a thermoplastic contamination pattern.

In accordance with another embodiment, the present invention can be characterized as a method comprising providing at least one sensor; detecting a plurality of parameters in a thermoplastic using the at least one sensor; generating a plurality of outputs in response to the detecting; and characterizing a percentage of post-consumer recycled thermoplastic content in the thermoplastic as a function of the plurality of outputs having been generated and a thermoplastic percentage of post-consumer recycled content (% PCR) pattern.

In accordance with a further embodiment, the present invention can be characterized as a method comprising detecting a plurality of parameters in a thermoplastic using at least one sensor; storing a set of thermoplastic pattern signatures in response to the detecting; and characterizing the thermoplastic as a function of the storing and a thermoplastic pattern signature.

BRIEF DESCRIPTION OF THE DRAWINGS

The above and other aspects, features and advantages of several embodiments of the present invention will be more apparent from the following more particular description thereof, presented in conjunction with the following drawings.

Figure 1:
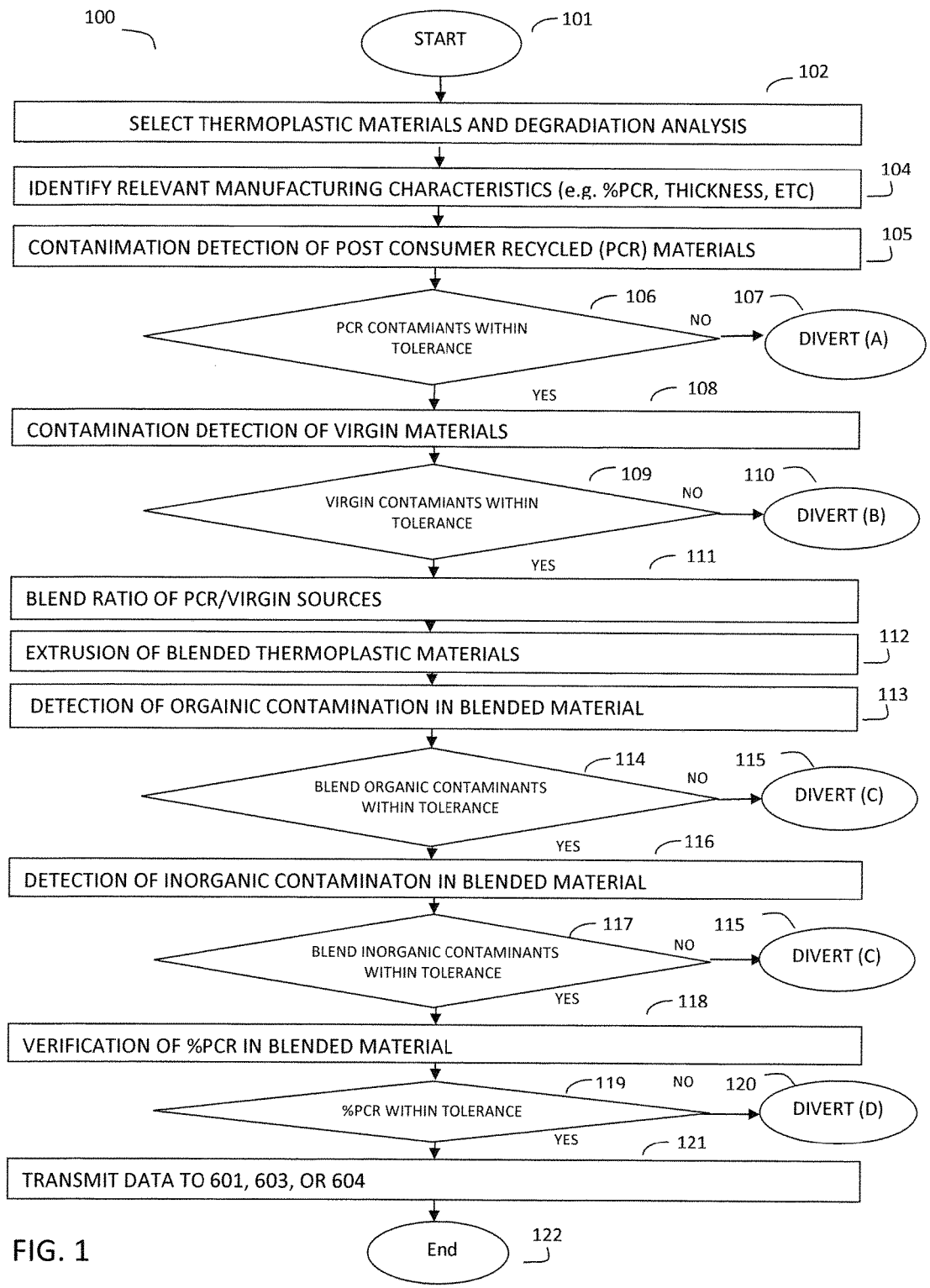
FIG. 1 is a flow diagram of an exemplary embodiment of a thermoplastic extrusion process in accordance with the present invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

The following description is not to be taken in a limiting sense, but is made merely for the purpose of describing the general principles of exemplary embodiments. The scope of the invention should be determined with reference to the claims.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

The embodiments presented herein address the various problems associated with recycling thermoplastics, for example: a) is the finished product safe for human use such as packaging food products, pharmaceuticals, and other plastic products such as electronics, clothing, and children's toys; b) is the claimed percentage of post-consumer recycled thermoplastic (% PCR) a valid claim; c) are the health/safety and the percentage of recycled thermoplastic content claims documented and thus verifiable claims?

Systems and methods for the detection, characterization, and verification include a plurality of methods for detecting, characterizing, and verifying organic (e.g., volatile organic compounds) and inorganic contaminants (e.g., metallic content) in virgin, recycled, and blended/ratios of virgin to recycled thermoplastic materials. In general terms, a method in accordance with one embodiment discussed herein consists of the following steps: (1) selection of virgin and recycled thermoplastic materials to be used in a finished product by a thermoplastic conversion process; (2) identification of relevant conversion line manufacturing and thermoplastic characteristics; (3) real-time assessment of organic (e.g., volatile organic compounds) and inorganic contamination (e.g., metallic content) content in the post-consumer recycled thermoplastic materials, the virgin thermoplastic material, and the finished thermoplastic product; (4) real-time validation of the percentage of recycled post-consumer thermoplastic (% PCR) in the finished product as specified during the manufacturing process; and (5) validation of the entire process by comparing test thermoplastic pattern signatures with digitally stored thermoplastic pattern signatures. A plurality of methods produces a unique pattern signature or identification (fingerprint) of finished thermoplastic materials. Storing and retrieving thermoplastic pattern signatures provide documentation for thermoplastic content certification and verification of certification.

There are several unique features of embodiments of the present invention: a) detection systems are guided by computer driven mathematical models and neural networks and computer-control systems; b) detection of organic (e.g., volatile organic compounds) and in organic (e.g., metallic content) contamination and % PCR in real-time, are compared to specific tolerances, with materials outside the specific tolerances being diverted for other uses; c) all data arrays and thermoplastic pattern signatures are stored (documented) either on the conversion line, the plant, or the plant complex servers; d) the stored data arrays and patterns serve as a signature or "finger print", a unique identification (ID) tying the finished thermoplastic product to the conversion line's manufacturing data such as date/time of production to measurements of organic (e.g., volatile organic compounds) and inorganic contamination (e.g., metallic content), and target level of % PCR. All relevant data, information, and pattern signatures are digitally stored. Storing and retrieving thermoplastic identification patterns (signatures) provide documentation for thermoplastic content certification and verification of certification.

Thermoplastic pattern signatures yield unique identification that is useful for truth in advertising (regarding the amount of recycled material) and health and safety certification, and verification of certification.

Safety of thermoplastic materials is determined by detection, characterization, and verification of organic and inorganic contamination within virgin thermoplastics, post-consumer recycled thermoplastics, and blends of virgin and post-consumer recycled thermoplastics.

Detection of organic and inorganic contamination within virgin thermoplastics, post-consumer recycled thermoplastics, and blends of virgin and post-consumer recycled thermoplastics is determined by means of a sensor to detect multiple types of contaminants or multiple sensors that detect different types of contaminants.

Characterization of organic and inorganic contamination within virgin thermoplastics, post-consumer recycled thermoplastics, and blends of virgin and post-consumer recycled thermoplastics is determined by means of pattern recognition of data obtained from a sensor to detect multiple types of contaminants or from multiple sensors that detect different types of contaminants.

Verification of organic and inorganic contamination pattern signatures within virgin thermoplastics, post-consumer recycled thermoplastics, and blends of virgin and post-consumer recycled thermoplastics is determined by means of comparing test thermoplastic contamination pattern signatures with digitally stored thermoplastic contamination pattern signatures.

Accuracy of claimed percentages of post-consumer recycled material is determined by detection, characterization, and verification of claimed percentages of post-consumer recycled thermoplastics within blends of virgin and post-consumer recycled thermoplastics.

Detection of percentages of post-consumer recycled material in blends of virgin and post-consumer recycled thermoplastics is determined by means of a sensor to detect multiple levels of percentages of post-consumer recycled material in blends of virgin and post-consumer recycled thermoplastics or multiple sensors that detect different levels of percentages of post-consumer recycled material in blends of virgin and post-consumer recycled thermoplastics.

Characterization of percentages of post-consumer recycled material in blends of virgin and post-consumer recycled thermoplastics is determined by means of pattern recognition of data obtained from a sensor for the detection of multiple levels of percentages of post-consumer recycled material in blends of virgin and post-consumer recycled thermoplastics or from multiple sensors that detect different levels of percentages of post-consumer recycled material in blends of virgin and post-consumer recycled thermoplastics.

Verification of the accuracy of percentages of post-consumer recycled material in blends of virgin and post-consumer recycled thermoplastics is determined by means of comparing test blends of thermoplastic materials pattern signatures with digitally stored blends of thermoplastic pattern signatures.

Embodiments of the present invention refer generally to systems and methods for recycled thermoplastics detection, characterization, and verification of advertised % PCR claims and health and safety claims in finished thermoplastic products.

Referring to FIG. 1, shown is a flow diagram of an exemplary embodiment of a thermoplastic extrusion process in accordance with the present invention. The process starts 101 with materials selection and degradation analysis of 102 post-consumer recycled thermoplastic material such pellets or particles of post-consumer recycled polyethylene terephthalate (RPET). Recycled materials have not only gone through the waste stream (post-consumer) but may also have been previously recycled, perhaps more than once. Degradation increases as a number of times (cycles) a thermoplastic material is recycled/reprocessed. Degradation analysis of selected materials 102 is investigated by measuring properties of the selected materials including but not restricted to mass flow index and other properties such as tensile and impact strength. Mass flow index is determined according to ASTM D-1238-86 with an extrusion plastometer Davenport model 3. Tensile measurement is found according to ASTM D-638-87 in an Instron 1122 testing machine. Impact strength is given according to ASTM D-256-87 in a Ceast 6545/000 pendulum impact tester.

Next, relevant manufacturing characteristic data 104 is collected. This data includes but are not restricted to the physical plant address, the conversion line address, a date and time stamp, the desired blend/ratio of virgin to recycled content (% PCR), source of virgin material, source of post-consumer recycled material, degradation of PCR, and characteristics of the conversion process. Example characteristic data 104 for an extrusion conversion process includes but is not restricted to torque of screw, screw speed, horse power at pump, melt pressure, melt temperature, intrinsic viscosity, die temperature, nozzle temperature, nozzle pressure, thickness of thermoplastic materials.

In accordance with the present embodiment, multiple sensors detect parameters indicative of levels of contamination in the post-consumer recycled (PCR) thermoplastic material 105. The same contamination detection methods are applied to virgin 108 and blended thermoplastic materials 113. Sensors also detect parameters indicative of the percentage of recycled thermoplastic material in the finished product 118.

In accordance with the present embodiment, detection of post-consumer recycled thermoplastic contamination 105 is followed by a decision point 106 with two options: 1) continue processing the thermoplastic materials; 2) divert the materials for future consideration. Processing continues if the level of contamination is within tolerance; otherwise the thermoplastic materials are diverted for further consideration 107. Detection of virgin thermoplastic contamination 108 is followed by a decision point 109 with two options: 1) continue processing the thermoplastic materials; 2) divert the materials for future consideration. Processing continues if the level of contamination is within tolerance; otherwise the thermoplastic materials are diverted for further consideration 110. The blend of virgin and recycled thermoplastic material is extruded 112. Detection of the extruded blended thermoplastic contamination 113 and 116 is followed by a decision point 114 and 117 respectively with two options: 1) continue processing the thermoplastic materials; 2) divert the materials for future consideration. Processing continues if the level of contamination is within tolerance; otherwise the thermoplastic materials are diverted for further consideration 115.

In the present embodiment, verification of intended blend, the % PCR 118 is followed by a decision point 119 with two options: 1) continue processing the thermoplastic materials; 2) divert the materials for future consideration. Processing continues if the target (e.g., 25%) level of % PCR is within tolerance (e.g., 23%-27%); the thermoplastic materials are diverted for further consideration if the levels of % PCR exceed pre-specified thresholds 120.

In various embodiments of this invention, the sequential order of the steps and decision points may vary. For example, the detection of inorganic (e.g., metallic) content 116 is not restricted to the finished product (blended production material) but may also be done on virgin thermoplastics and post-consumer recycled thermoplastics.

The detection of contamination in thermoplastics includes at least one contamination sensor to detect multiple types of contaminants or multiple sensors that detect different types of contaminants; and test for acceptable levels of contaminants. The example embodiment in 701 of FIG. 7 employs multiple sensors, the sensor array. In the example embodiment, detection of contamination is followed by a decision point 106 (is the level of recycled post-consumer thermoplastic contamination within tolerance?) and decision point 109 (is the level of virgin thermoplastic contamination within tolerance?) and decision point 114 (is the level of blended thermoplastic contamination within tolerance?) with two options: 1) continue processing the thermoplastic materials; 2) divert the materials for future consideration. Processing continues if the level of contamination is within tolerance; the thermoplastic materials are diverted for further consideration if the levels of contamination exceed a pre-specified threshold.

In accordance with the current embodiment, acceptable levels of contamination for post-consumer recycled thermoplastics 106, virgin thermoplastics 109, and blends of virgin to post-consumer recycled thermoplastics 114 are defined by the Code of Federal Regulations (CFR) which is the codification of the general and permanent rules and regulations published in the Federal Register by the executive departments and agencies of the federal government of the United States. The CFR is published by the Office of the Federal Register, an agency of the National Archives and Records Administration (NARA). Acceptable levels of contamination in thermoplastics 106, 109, 114 are not restricted to the above definitions and may differ depending upon local and state laws.

The detection of inorganic contamination (e.g., metallic content) 116 in thermoplastics includes at least one sensor to detect inorganic content and test for acceptable levels of inorganic content. The example embodiment (800 of FIG. 8) employs x-ray fluorescent for the detection of metallic content in thermoplastic materials. In the example embodiment, detection of metallic content is followed by a decision point 117 (are the levels of metallic content in thermoplastic materials within tolerance?) with two options: 1) continue processing the thermoplastic materials; 2) divert the materials for future consideration. Processing continues if the level of metallic content is within tolerance; the thermoplastic materials are diverted for further consideration if the levels of metallic content exceed a pre-specified threshold 115. Acceptable levels of inorganic contamination (e.g., metallic) content 117 may be defined by the Code of Federal Regulations (CFR), the codification of the general and permanent rules and regulations published in the Federal Register by the executive departments and agencies of the federal government of the United States.

The verification of % PCR, the blend or ratio of virgin to post-consumer recycled % PCR thermoplastics 118 includes at least one sensor to detect % PCR and test for deviation from the target level of % PCR. The example embodiment of this invention (900 of FIG. 9) employs ultraviolet-visible spectroscopy (UV-Vis) to measure to absorption spectroscopy in the ultraviolet-visible spectral region. In the example embodiment, UV irradiation and the detection of transmitted light is performed with a Perkin Elmer optoelectronics xenon flash light (LS-LX) FX 1160 and a Carl Zeiss MCS CCD diode array detector. The detection takes place with a Nikon stereomicoscope. The vibration band of the double bounds is obtained via the Bruker Multiram Raman number 4 spectrometer. Detection of % PCR is followed by a decision point 119 (is the level of % PCR within tolerance?) with two options: 1) continue processing the thermoplastic materials; 2) divert the materials for future consideration. Processing continues if the level of % PCR is within tolerance; the thermoplastic materials are diverted for further consideration if the levels of % PCR exceed pre-specified bounds 120. The range of acceptable levels as determined in decision point 119 of % PCR is calculated by the target value (e.g. 50% recycled) plus/minus acceptable % ERROR. Typical % ERRORs includes two to three percentage points although this depends upon relevant circumstances. At the present there are no CFRs specifying the accuracy of % PCR claims made by manufacturers of post-consumer recycled thermoplastic products.

At the conclusion, manufacturing characteristics data and other relevant data collected throughout the thermoplastic conversion process are transmitted 121 to the microcomputer and communication system (brain) 601 for processing, storage, and communications. In a single conversion line inorganic (e.g. metallic), organic (e.g. volatile organic compounds), and % PCR signatures of thermoplastic materials are stored and processed in the brain 601. In a plant (multiple conversion lines), the inorganic (e.g. metallic), organic (e.g. volatile organic compounds), and % PCR signatures of thermoplastic materials are stored and processed in the plant server 603. In a plant complex (multiple thermoplastic plants) embodiment, inorganic (e.g. metallic), organic (e.g., volatile organic compounds), and % PCR signatures of thermoplastic materials are stored and processed in the plant complex server 604. In some embodiments, storage and processing occurs in all three servers: the brain 601, the plant server 603, and the plant complex server 604. In the present embodiment, the said steps/components of the thermoplastic conversion process the components coexist within a physical plant. In other embodiments, the said steps/components may be physically separate, may be a virtual conversion line. For example recycled thermoplastic materials for the detection of contamination in virgin thermoplastics 108, 109, and 110 may reside in Illinois and virgin thermoplastic materials for steps detection of degradation 102 and contamination in post-consumer recycled thermoplastics 105, 106, and 107 may reside in Canada. In various embodiments of this invention, the sequential order of the steps and decision points may vary.

In other embodiments this invention the thermoplastic conversion process applies to but is not restricted to innovative thermoplastic conversion processes (lines) such as injection molding, compression molding, transfer molding, rotational molding, extrusion, blow molding, blown film extrusion, thermoforming, calendaring fibering, foaming, laminating, etc. Types of thermoplastics include but are not restricted to any type of thermo softening plastic, a polymer that becomes pliable or moldable above a specific temperature, and returns to a solid state upon cooling such as a polyethylene terephthalate (PET), a polyethylene, a polypropylene, a polystyrene, a poly methylmethacrylate, a polycarbonate, an addition poly merthermoplastic or a condensation polymer thermoplastic.

Figure 2:
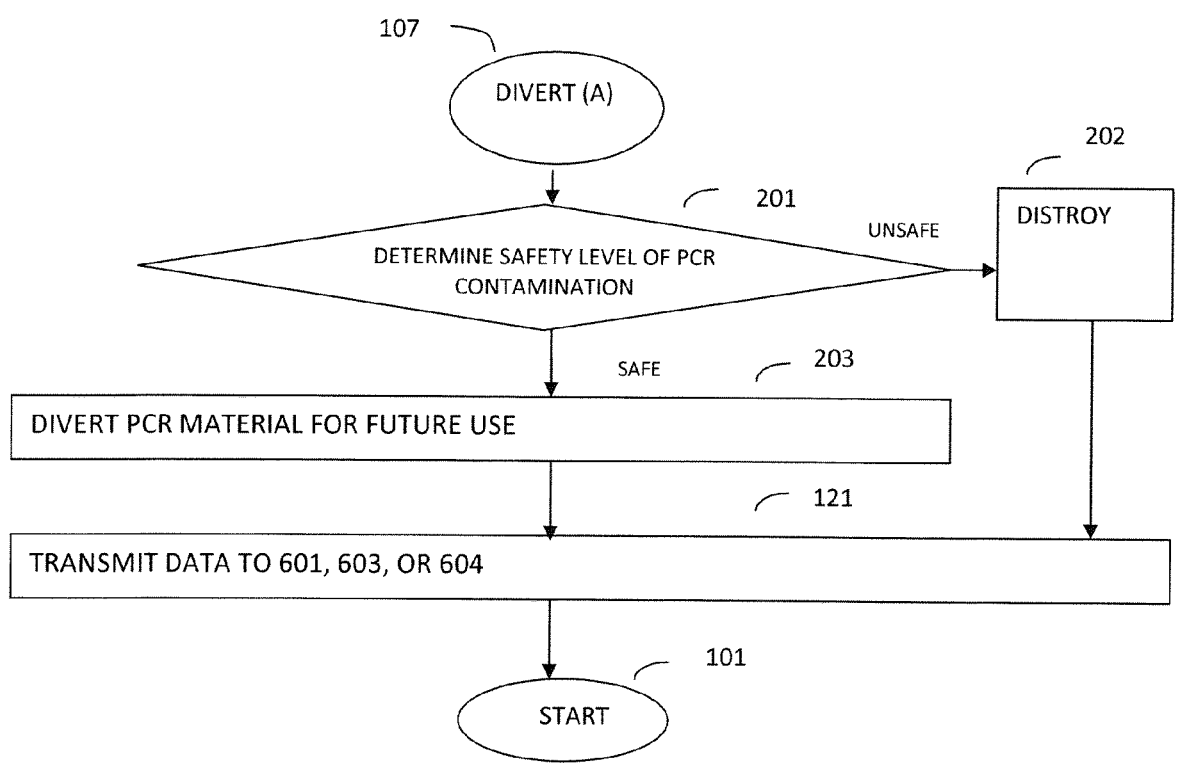
FIG. 2 is a flow chart of a method 200 for diverting post-consumer recycled thermoplastics that are outside of CFR tolerances such that such post-consumer recycled thermoplastics are again evaluated for safety 201 in accordance with a variation of the embodiment shown in FIG. 1.

Referring next to FIG. 2, a flow chart is shown of a method 200 for diverting post-consumer recycled thermoplastics that are outside of CFR tolerances such that such post-consumer recycled thermoplastics are again evaluated for safety 201 in accordance with a variation of the embodiment shown in FIG. 1. In some instances current CFRs may be viewed as too lenient whereas the individual manufacturer or buyer of the thermoplastic finished product may have stricter standards and thus the safety level of contaminated PCR 201 may be checked against the manufacturer's or buyer's safety standards. Unsafe product 202 maybe destroyed while safe product 201 may be diverted again or returned to stock for potential future use 203. Relevant data 121 are communicated to the brain 601, the plant server 603, or the plant complex server 604.

Figure 3:
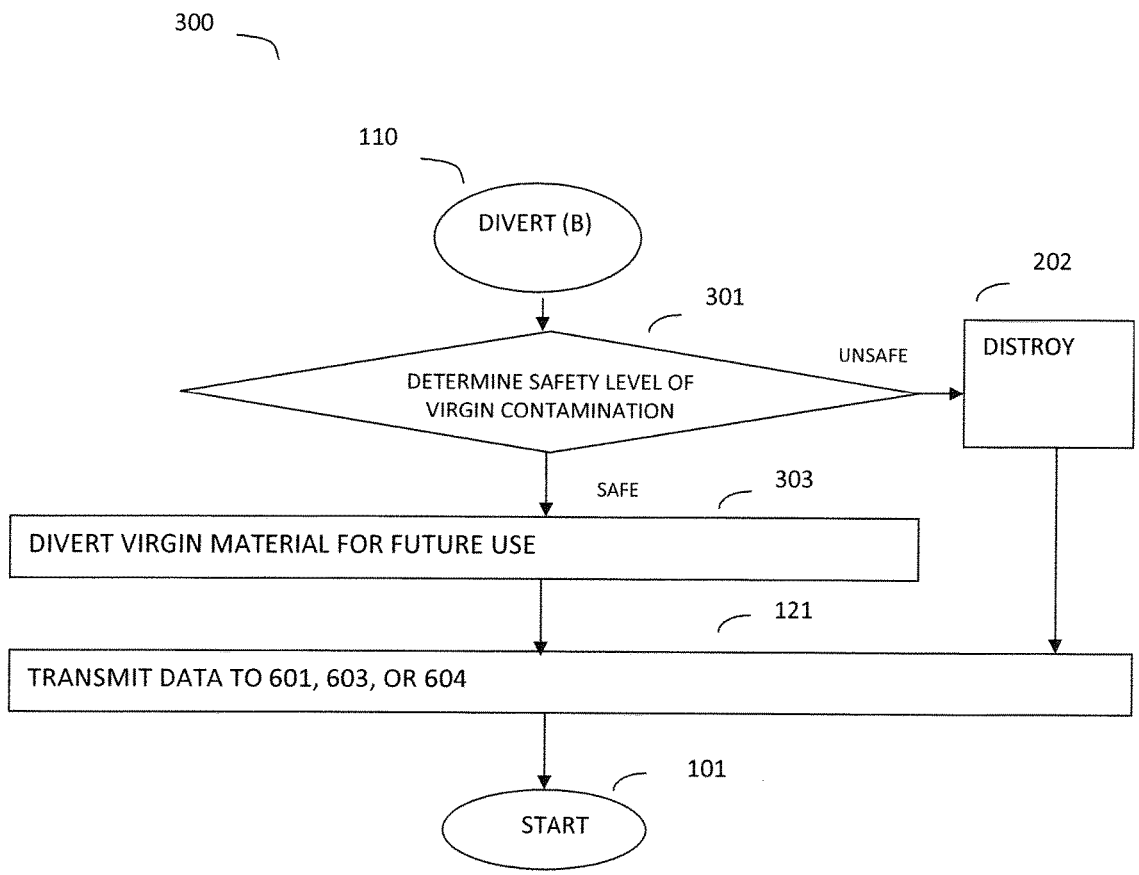
FIG. 3 is a flow chart of a method 300 for diverting virgin thermoplastics that are outside of CFR tolerances such that such virgin thermoplastics are again evaluated for safety in accordance with a further variation of the embodiment of FIG. 1.

Referring to FIG. 3, a flow chart is shown of a method 300 for diverting virgin thermoplastics that are outside of CFR tolerances such that such virgin thermoplastics are again evaluated for safety in accordance with a further variation of the embodiment of FIG. 1. In some instances current CFRs may be viewed as too lenient whereas the individual manufacturer or buyer of the thermoplastic finished product may have stricter standards and thus the safety level of contaminated virgin thermoplastics 301 may be checked against the manufacture's or buyer's safety standards. Unsafe product 302 may be diverted again or returned to stock for potential future use 303. Relevant data 121 are communicated to the brain 601, the plant server 603, or the plant complex server 604.

Figure 4:
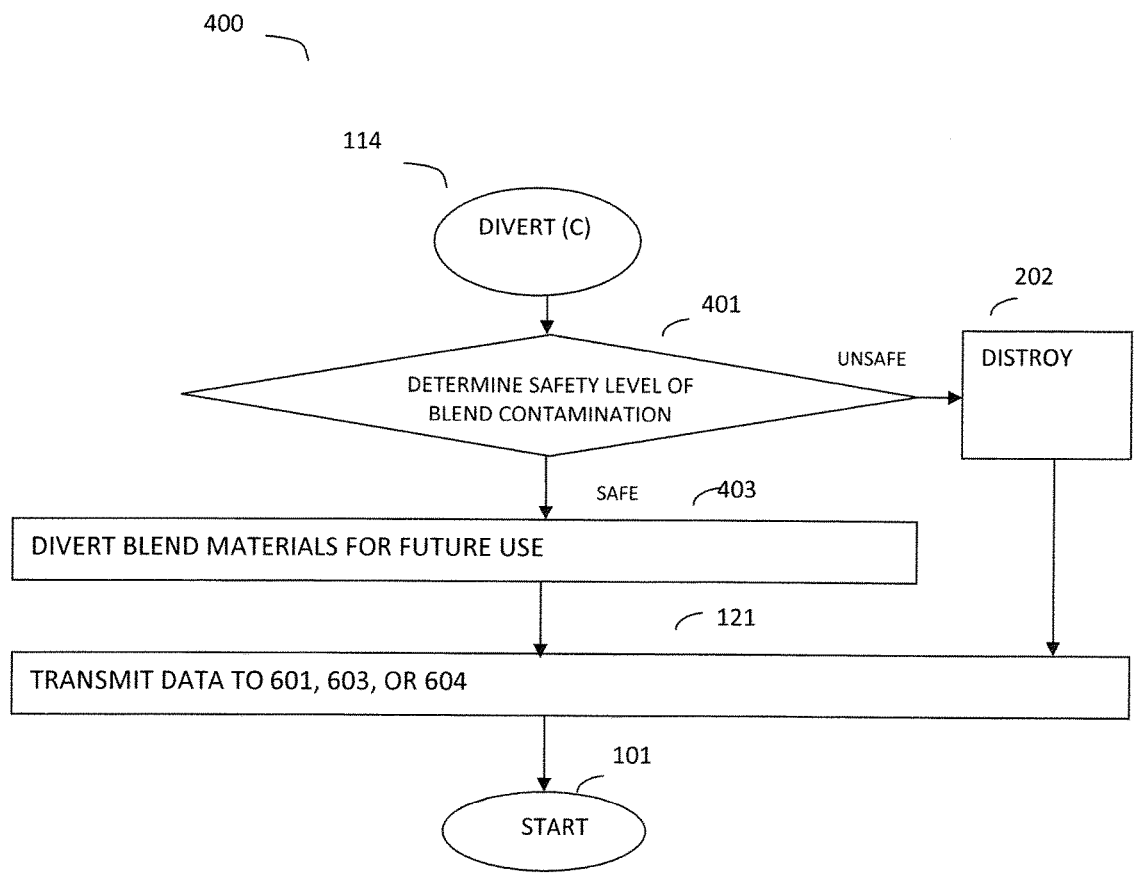
FIG. 4 is a flow chart of a method 400 for diverting blends of virgin to post-consumer recycled thermoplastics that are outside of CFR tolerances such that such blends of virgin to post-consumer recycled thermoplastics are again evaluated for safety.

Referring to FIG. 4, a flow chart is shown of a method 400 FIG. 4 for diverting blends of virgin to post-consumer recycled thermoplastics that are outside of CFR tolerances such that such blends of virgin to post-consumer recycled thermoplastics are again evaluated for safety. In some instances current CFRs may be viewed as too lenient whereas the individual manufacturer or buyer of the thermoplastic finished product may have stricter standards and thus the safety level of contaminated blends of thermoplastics 401 may be checked against the manufacture's or buyer's safety standards. Unsafe product 402 may be checked against the manufacture's or buyer's safety standards. Unsafe product 402 may be diverted again or returned to stock for potential future use 403. Relevant data 121 are communicated to the brain 601, the plant server 603, or the plant complex server 604.

Figure 5:
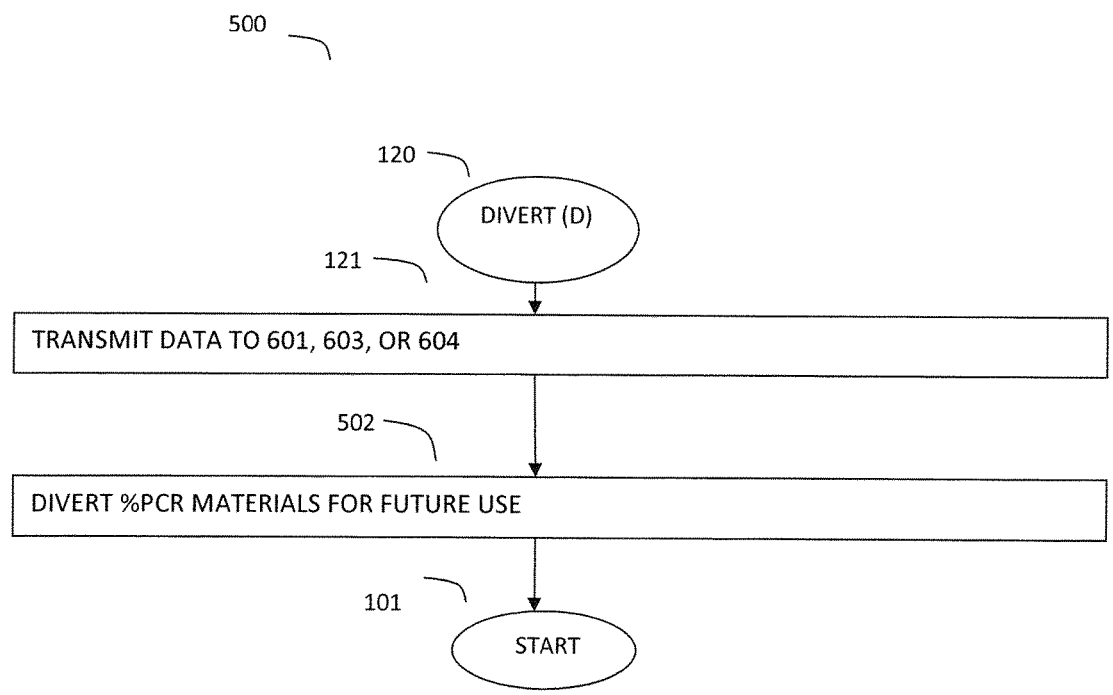
FIG. 5 is a flow chart of a method 500 for diverting blends of virgin to post-consumer recycled thermoplastics, % PCR, that are outside manufacturing specifications.

Referring to FIG. 5, a flow chart is shown of a method 500 in accordance with one variation of the embodiment of FIG. 1 for diverting blends of virgin to post-consumer recycled thermoplastics that are outside manufacturing specifications, the relevant data 121 are communicated to the brain 601, the plant server 603 or the plant complex server 604 and the incorrectly blended product is stored for future use 502. In other embodiments, the product may be recycled or sold as for a different purpose; or relabeled and used as is. For example, an intended 50% PCR finished product may be found to have too little PCR by 10% and thus may be relabeled as 40% PCR, etc.

Figure 6:
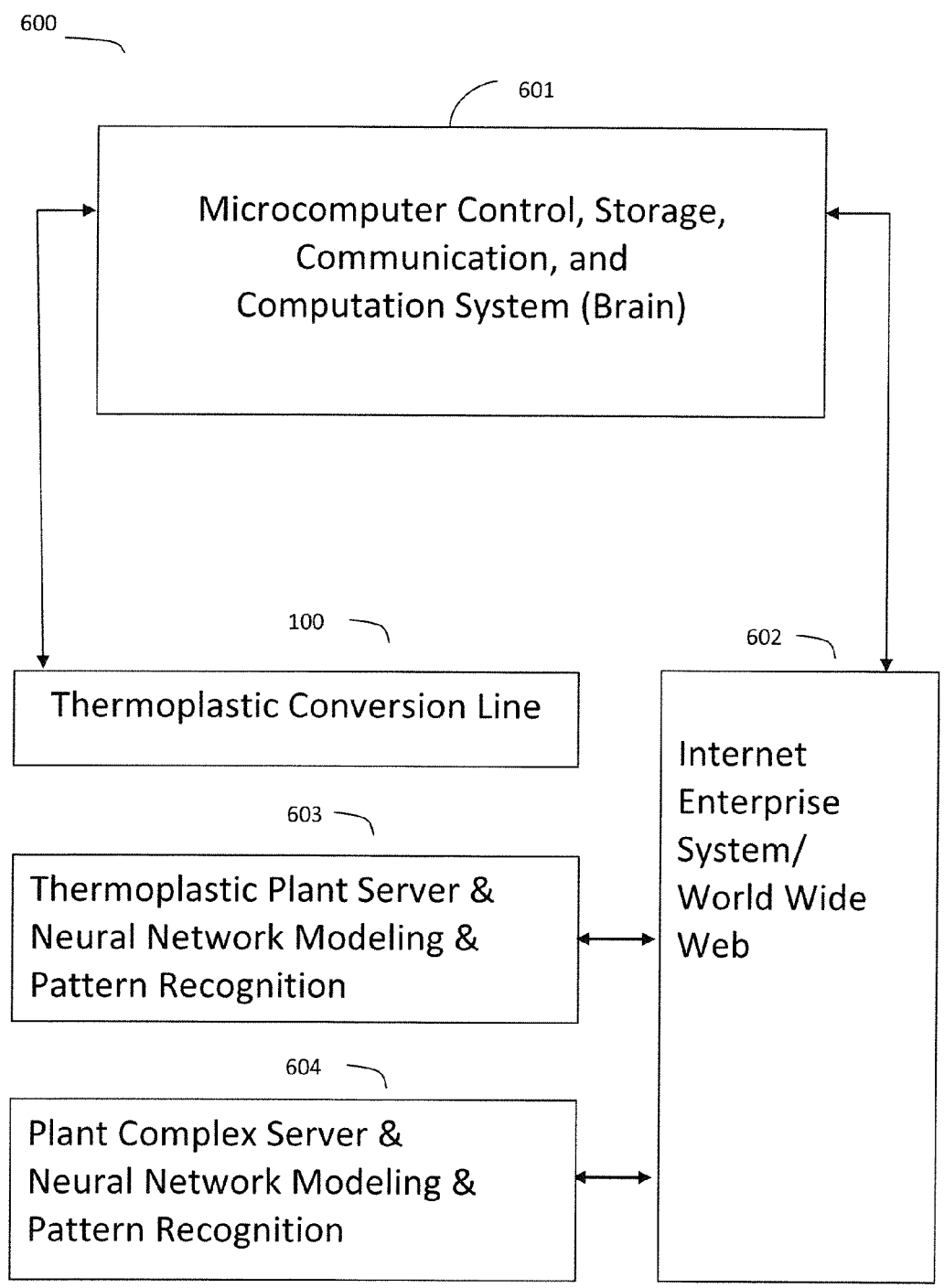
FIG. 6 is a block diagram of a general command and control system 600 in accordance with one variation for performing the method of FIG. 1.
Figure 7:
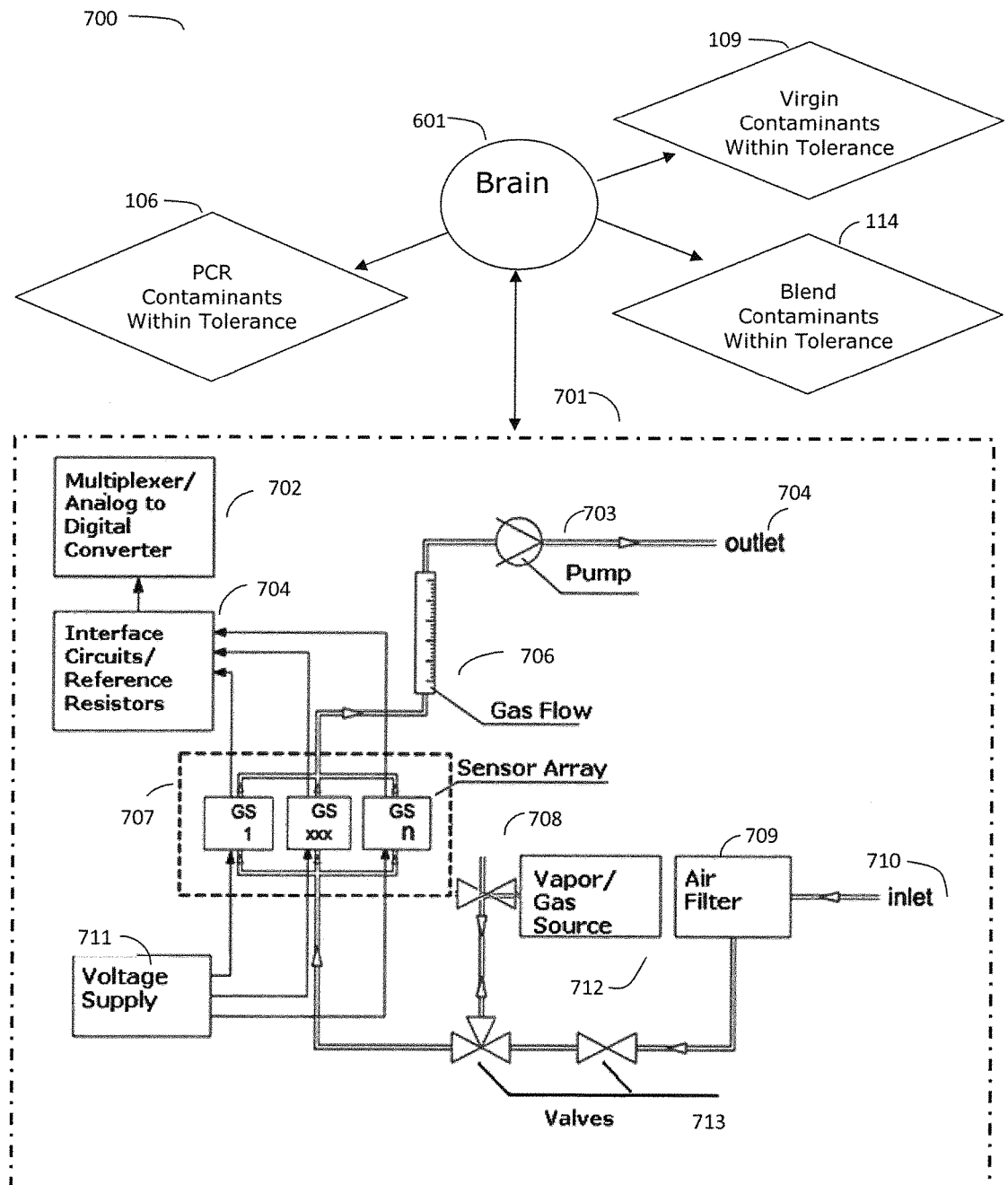
FIG. 7 is a block diagram of a system for multiple sensor detection of organic contamination in accordance with one variation of the embodiment of FIG. 6.

Referring to FIGS. 6 & 7, a block diagram is shown of a general command and control system 600 in accordance with one variation of the embodiment of FIG. 1 comprising microcomputer system computation system (also referred to herein as a brain) that controls operations and communications with thermoplastic conversion line, the plant server and the plant complex server. The present embodiment employs a microcomputer system 601. The brain 601 controls all relevant operations of the thermoplastic conversion line 100 including organic contamination detection of post-consumer recycled thermoplastics 105, tolerance checks 106, diversion 107, organic contamination detection of virgin thermoplastics 108, tolerance checks 109, diversion 110, organic contamination detection of blended thermoplastics 113, tolerance checks 114, diversion 115, inorganic contamination detection of blended thermoplastics 116, tolerance checks 117, diversion 115; verification of % PCR in blended thermoplastics 118, tolerance checks 119, diversion 120. The brain 601 controls information transmission among the conversion line 100, the plant server 603, and the plant complex server 604.

In other embodiments of this invention the brain 601 may include but is not restricted to a desktop computer, a laptop computer, a tablet, a pad, a Smartphone, or some other computational device. In the example embodiment, the conversion line brain 601 is physically attached to a conversion line 100 but in other embodiments it is a virtual device housed in a separate physical location. In the present embodiment, data storage is a magnetic hard drive but alternate embodiments may include but are not restricted to solid state storage or online or virtual storage systems. In the present example embodiment, communications among the brain 601 and relevant system components on the conversion line 100 consist of copper wire and optical fiber but other embodiments may include aluminum wire, wireless communications; thus other embodiments may not be restricted copper wire or optical fiber. In the present example embodiment, communications from a conversion line 100 to external servers 603 and the plant complex server 604 consists of but is not restricted to the Internet, a network system that employs the standard Internet protocol suite (TCP/IP). In the example embodiment, the servers in 603 and the plant complex server 604 are IBM System x3850 7143C3U 4U Rack Servers.

The brain 601, the plant server 603, and the plant complex server 604 include a computation component to process thermoplastic measurements via and artificial neural network analysis. In the example embodiment 701 of FIG. 7, the sensor array 707 detects various types and levels of contamination and using a trained Back-Propagation model. Back-Propagation neural networks yield a supervised predictive model which is developed by training sessions done in a controlled (lab) setting whereby known contaminants of interest are run and re-run through system 701 in repetitive fashion until the neural network model learns to correctly identify the test contaminants. Once the predictive neural network is trained, it is then used on the conversion line to detect the level of contamination in the virgin, recycled, and blended thermoplastic materials. These predictions are in the form of probabilities; e.g., the probability that the thermoplastic material contains at least 50 ppm benzene=0.95. The sensitivity values of each sensor in the sensor array create a thermoplastic contamination pattern signature or "fingerprint". The relationship between the sensor resistance 704 and the concentration of deoxidizing gas is expressed over a certain ranges of gas concentration: $R_s = K*C^{-\beta}$, where K is a constant, C is gas concentration, and $\beta$ is the slope of the $R_s$ curve. The relationship of sensor resistance to gas concentration is linear on a log scale within certain ranges, from a few ppm to several thousand ppm and nonlinear thereafter. Different sensors have different resistance 704 values and thus sensor sensitivity is expressed as a ratio of sensor resistance in various concentrations of gases $R_s$ over resistance in a certain concentration of a target gas $R_o$. A sensor sensitivity's ranges from a minimum value=0% and maximum value=100%. Thus an organic contamination signature or "fingerprint" as defined by 15 sensors with 100 sensor sensitivity units yields a potential of $100^{15} = 1E+30$ possible signatures.

In the present embodiment of the sensor system 701, the inputs into the hidden neurons in the artificial neural network correspond to sensors in the sensor array 707. The sensor array interfaces with thermoplastic gases/vapors; outputs from the neurons provide the predictions of the analysis. Hidden neurons are mathematical abstractions and are hidden from view but are digitally stored in the brain 601 the plant server 603, and the plant complex server 604. The network function is given by the interconnections between the sensor array inputs, the neurons, and the outputs, the predicted thermoplastic contaminants, and the contamination pattern signature. Each sensor input to a neuron has a weight factor of the function that yields the strength of connection and thus the contribution of that connection to other neurons. During the training session, the artificial network's connection weights are adjusted until they accurately predict the desire type and level of thermoplastic contamination.

In general terms, artificial neural networks are massively parallel distributed processors consisting of simple processing units, which enable the storing of experiential knowledge. Knowledge of contamination is acquired by the network from exposure to contamination through a learning process. Inter-neuron connection strengths (synaptic weights) are used to store the acquired knowledge. Thus, in the example embodiment, the trained neural network by making use of this acquired knowledge is able to detect the types and levels of thermoplastic contamination.

Figure 11:
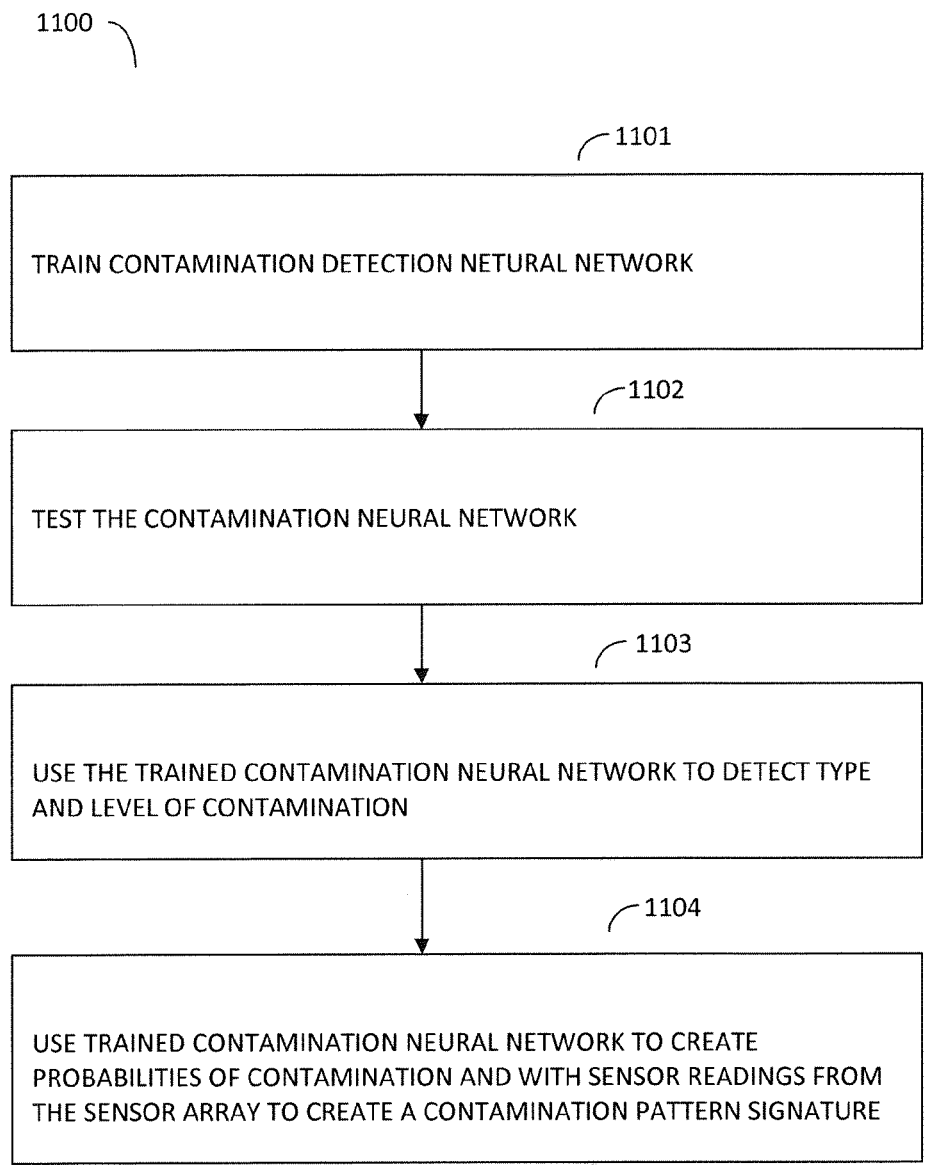
FIG. 11 is a block diagram of a system for training, testing, and using a neural network model in accordance with one variation of the embodiment of FIG. 6 and FIG. 7.

Referring next to FIG. 11, a block diagram is shown of a Back-Propagation algorithm in accordance with a variation of the embodiment of FIG. 6. The Back-Propagation algorithm is used to train a multi-layer feed-forward network with differentiable transfer functions to perform function approximation for prediction, pattern association, and pattern classification. The Back-Propagation model is a process by which derivatives of network error, with respect to network weights and biases, are computed. The training of artificial neural networks by Back-Propagation takes three steps:

1. The feed-forward of the training pattern from the inputs of the contamination sensor array.
2. The calculation and Back-Propagation of the associated error of prediction, and
3. The adjustment of the weights to maximize the outputs, the prediction of the type and level of contamination.

Various embodiments of this invention may require experimental results to develop a neural network that accurately predict the type and level of thermoplastic contamination; this is particularly true with supervised neural networks. Alternate embodiments of this invention may vary in the neural network architecture, training functions, training algorithms and other parameters, followed by the training processes and evaluation methods. After the network has learned to accurately predict the type of level of contamination, the system is then ready for use. The process of creating artificial neural networks for the prediction of type and level of thermoplastic contamination can, therefore, be summarized in terms of the following steps, 1. Training of the neural networks: this includes but is not restricted to the choice of its architecture, training functions, training algorithms, and parameters of the network, 1101.
2. Tests of the trained networks; the evaluation of network's ability to predict the type and level of thermoplastic contamination, 1102.
3. Use of the successfully trained neural networks to detect the type and level of thermoplastic contamination, 1103.
4. Use of the successfully trained neural networks to create the thermoplastic organic contamination pattern signatures, 1201 of the system 1200.

In general, the above said steps not only apply to organic contamination pattern signatures but in other embodiments of this invention, they may also be applied to inorganic contamination pattern signatures, 1202 and to % PCR pattern signatures, 1203.

The sensors' sensitivity to various contaminants, the probabilities of prediction, and the actual predicted contaminants define the organic contamination pattern signature, 1104.

The current embodiment includes but is not restricted to the feed forward the Back-Propagation model. In other embodiments, other supervised neural network models may be applied such as the simple perceptron, the adaline (adaptive linear neuron), the Boltzman/Cauchy machine, the radial basis function network, the brain-state-in-a-box, the counterpropagation method, the neocognition method, and the adaptive resonance theory 2.

Figure 14:
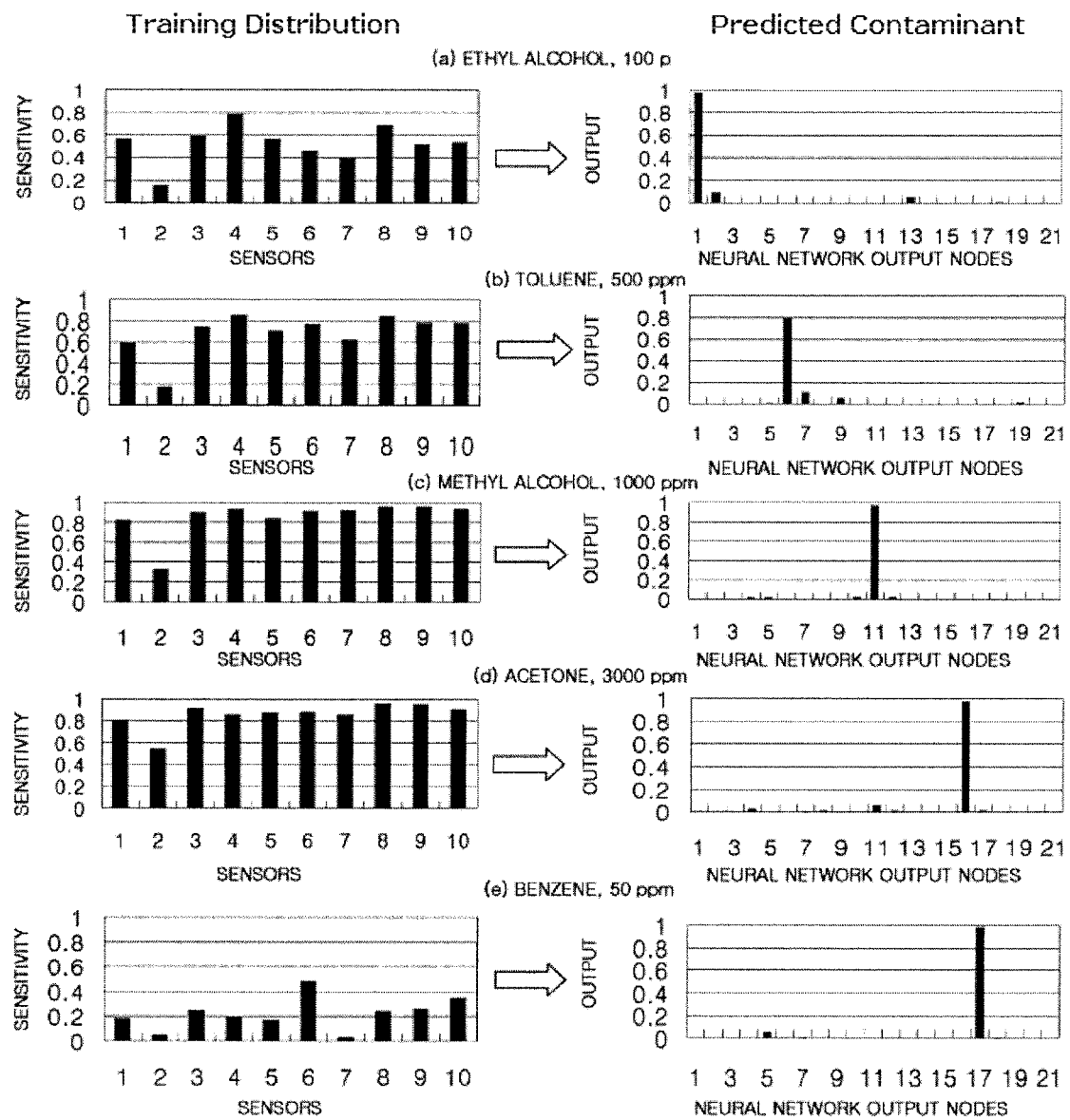
FIG. 14 is a series of graphs of neural network training patterns and prediction probabilities of contamination in thermoplastics.

FIG. 14 presents an example application of predicting select types and levels of organic volatile compound contamination (Lee, D. S., Y. Tae Kim, J. K Jung, J. W Lim, J. S. Huh, and D. D. Lee, 2001). In this research a ten sensor array integrated on a substrate was trained to recognize different types of volatile organic compounds: benzene, toluene, ethyl alcohol, methyl alcohol, and acetone. The ten sensor array consisted of gas-sensing materials using $SnO2$ as the base material along with a heating element based on a meandered platinum layer deposited on the substrate. The sensors on the sensor array were designed to produce a uniform thermal distribution and to show sensitivity to low concentrations of the above contaminants. The sensing signals of the array were input into a multi-layered artificial neural network using the Back-Propagation algorithm. The first column of FIG. 14 presents the training distribution of sensitivities for the ten sensors for each of the five experimental contaminants; the second column of FIG. 14 presents the contaminant predicted by the trained neural network model.

Additionally, there exists an array of unsupervised neural networks and related tools useful in pattern recognition such as adaptive resonance theory 1, Hopfield networks, bidirectional associative memory, temporal associative memory, fuzzy associative memory, learning vector quantizer, Kohonen self-organizing map, generative topological map, time adaptive self-organizing map, growing self-organizing map, elastic mapping, principle components, K-means cluster analysis, and hierarchical cluster analysis.

The mathematics and algorithms for artificial neural networks are provided by Fausett, L. (2006), Fundamentals of Neural Networks: Architectures, Algorithms, and Applications, Pearson, ISBN: 9788131700532. Applications to polymer composites are given in Zhang, Z., and K. Friedrich (2003), "Artificial neural networks applied to polymer composites: a review," Composites Science and Technology, Vol. 63, pp. 2029-2044, ISSN: 0266-3538.

Referring back to FIG. 7, a block diagram in accordance with one variation of the embodiment of FIG. 6 is shown. In the variation shown, the sensor array 707 in FIG. 7 consists of semiconducting metal oxide sensors as described in Kanan, S. M., O. M. El-Kadri, I. A. Adu-Yousef, and M. C. Kanan (2009). In some embodiments, resistance modulation semiconducting metal oxide sensors are mounted inside an airtight, flow-type test chamber. The chambers are made of aluminum (or of some other material) so that the chemical reactions of thermoplastic contaminants and oxygen on the surface of sensing material do not produce intermediate products that affect responses of neighboring sensors. In some embodiments, the sensors are connected in parallel using Teflon-tubing (or of some other non-reactive material). This embodiment of the system and method allows for the simultaneous exposure of all sensors to the same thermoplastic gases 707. A voltage supply powers the sensor array 707. The volume and rate of alternating thermoplastic gas and filtered air flow is recorded by a gas flow meter 706. The chambers receive thermoplastic gas from an inlet 712 and are then flushed via an outlet 704 with filtered air 709 from an air inlet 710 and a vent 708. A pump 703 and the inlet 710, the outlet 704 and valves 718 are controlled by the brain 601. The interface circuits/reference resistors 704 measures resistance and a multiplexer/analog digital converter 702 converts the analog signals to digital signals which are sent to the brain 601 for analysis. In the example embodiment, detection of contamination is followed by the decision point 106 (is the level of recycled post-consumer thermoplastic contamination within tolerance?) and the decision point 109 (is the level of virgin thermoplastic contamination within tolerance?) and the decision point 114 (is the level of blended thermoplastic contamination within tolerance?) with two options: 1) continue processing the thermoplastic materials; 2) divert the materials for future consideration. Processing continues if the level of contamination is within tolerance; otherwise the thermoplastic materials are diverted for further consideration, if the levels of contamination exceed a pre-specified threshold.

In the example embodiment of this invention, the sensors of the sensor array are manufactured by Figaro Engineering Inc. who is an ISO 9001 and 14001 compliant company. Figaro Gas Sensors are solid-state devices composed of sintered metal oxides which detect gas through an increase in electrical conductivity when reducing gases are adsorbed on the sensor's surface. Other embodiments employ product from other manufacturers and some embodiments require custom built sensors.

Described in general terms, the invention employs mechanisms for the detection of contamination in post-consumer recycled, virgin, and blended thermoplastics, 701. In the example embodiment, a key component of 701 is the sensor array 707. The sensor array may include a mix of sensors and is not restricted to any one type of sensor. Possible sensors include headspace solid phase micro extraction gas chromatography mass spectrometry, PPB-Level sensors based on catalytic combustion, gas chromatography (GC)/mass spectroscopy with multiple-ion detector (MID), GC with FID (flame ionization detector), flame-photometric detector, ECD (electron capture detector), photo ionization detector (PID), flame ionization detector (FID), head-space GC, Pryrolyzer-GC/MC, time-of-flight MS (TOFMS), high presume liquid chromatography, Infrared spectroscopy, solid state sensors, semiconducting metal oxide sensors, transmission electron microscopy, Raman spectroscopy, light scattering, x-ray, x-ray diffraction, and x-ray fluorescent.

In other embodiments of this invention, an example sensor with multiple readings, suitable as inputs into a neural network model is the MIR 9000 LCD Multi-Gas Infrared GFC Analyzer distributed by Altech Environment U.S.A. This single sensor unit yields ten (10) readings/inputs into the neutral net.

Figure 8:
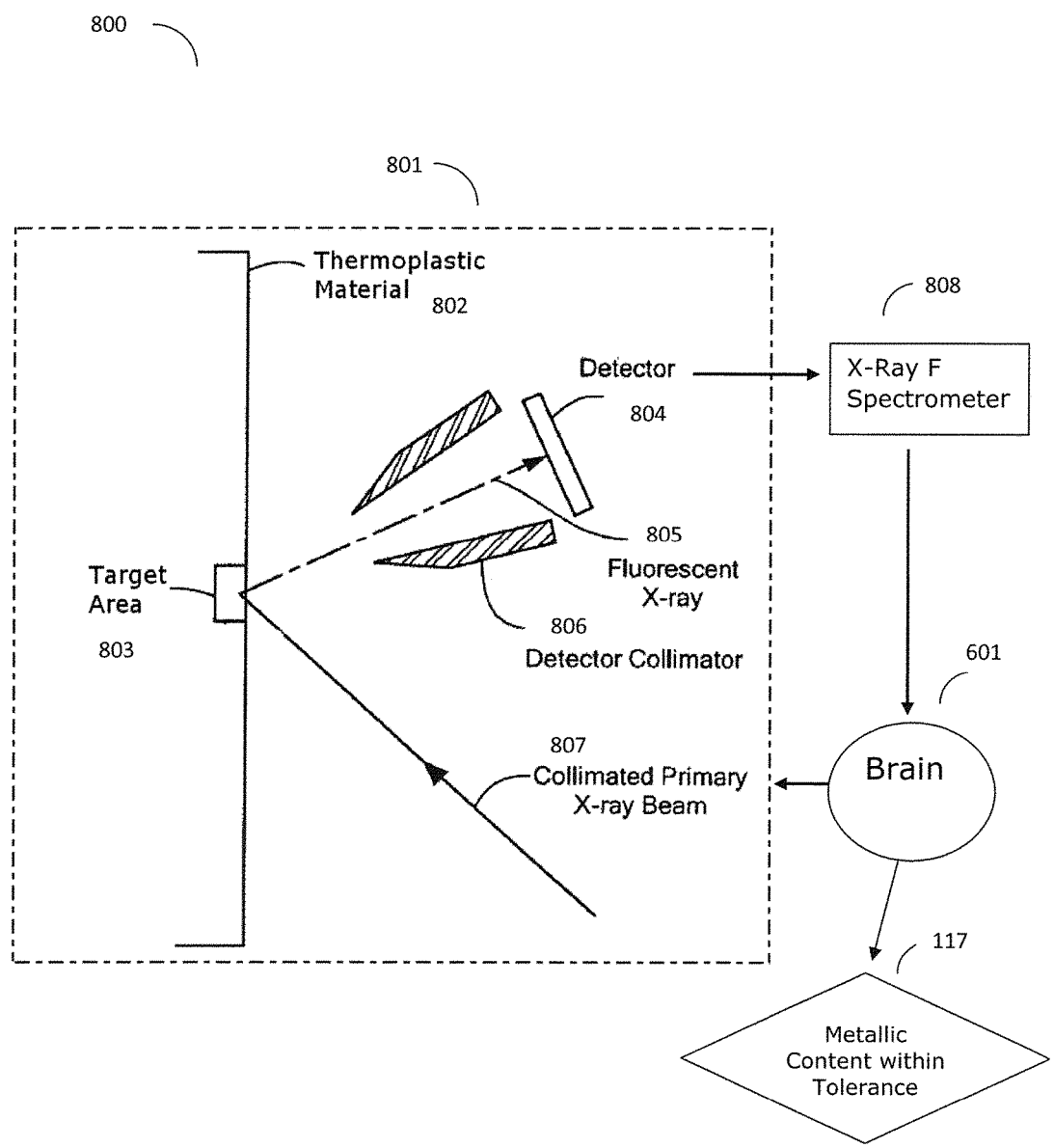
FIG. 8 is a schematic diagram of a system for detecting inorganic contamination in accordance with a variation of the embodiment of FIG. 6.

Referring to FIG. 8, shown is a schematic diagram of a system for testing thermoplastic material in accordance with a variation of the embodiment of FIG. 6. The California Health and Safety Code 25214.13 states that lead, mercury, cadmium, and hexavalent chromium are inorganic contaminants of particular concern. Described in general terms, the current embodiment of the invention employs x-ray fluorescence spectrometry for the detection of metallic content in post-consumer recycled, virgin, and blended thermoplastics 800. The brain 601 controls the collimated primary x-ray beam 807; this beam strikes the target area 803 of thermoplastic material 802. The fluorescent x-ray 805 strikes a detector 804 and a signal is sent from the detector 804 to an x-ray fluorescent spectrometer 808 and then from spectrometer 808 to back to the brain 601 and then to the decision point 117. In the example embodiment, detection of metallic content is followed by a decision point 117 (are the levels of metallic content in thermoplastic materials within tolerance?) with two options: 1) continue processing the thermoplastic materials; 2) divert the materials for future consideration. Processing continues if the level of metallic content is within tolerance; otherwise the thermoplastic materials are diverted for further consideration, if the levels of metallic content exceed a pre-specified threshold.

Alternate embodiments of the application of x-ray fluorescence for the detection of metallic content in thermoplastic material may be created with small devices manufactured by Thermo Scientific portable energy-dispersive x-ray fluorescence (EDXRF) analyzers and Skyray Instrument EDX Pocket III handheld X-rag Fluorescence Spectrometer. The EDX Pocket III detects n=70 elements.

The parts per million, ppm, for of each of the n elements defines an inorganic contamination pattern signature, 1202 of system 1200.

Other embodiments of this invention may employ various other methods of detecting inorganic compounds (e.g., metallic content) in thermoplastics including but not restricted to atomic absorption, inductively coupled plasma atomic emission, x-ray k-edge, passive gamma, passive neutron, neutron activation. Other embodiments of this invention may use multiple sensors of inorganic contamination and thus make use of both supervised and unsupervised neural network models.

Figure 9:
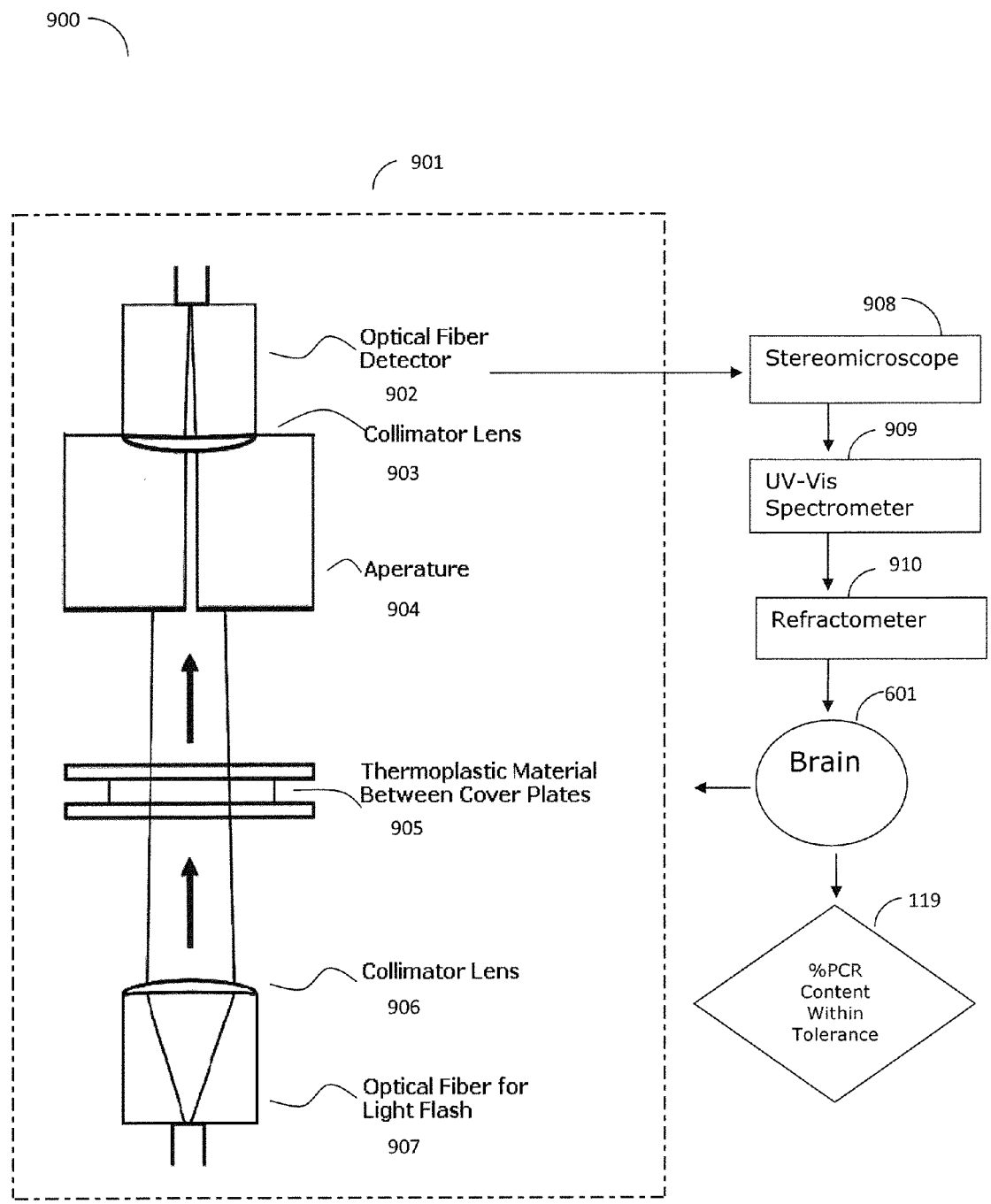
FIG. 9 is a schematic diagram of a system for detecting patterns of percentages of post-consumer recycled thermoplastics in accordance with one variation of the embodiment of FIG. 6.
Figure 10:
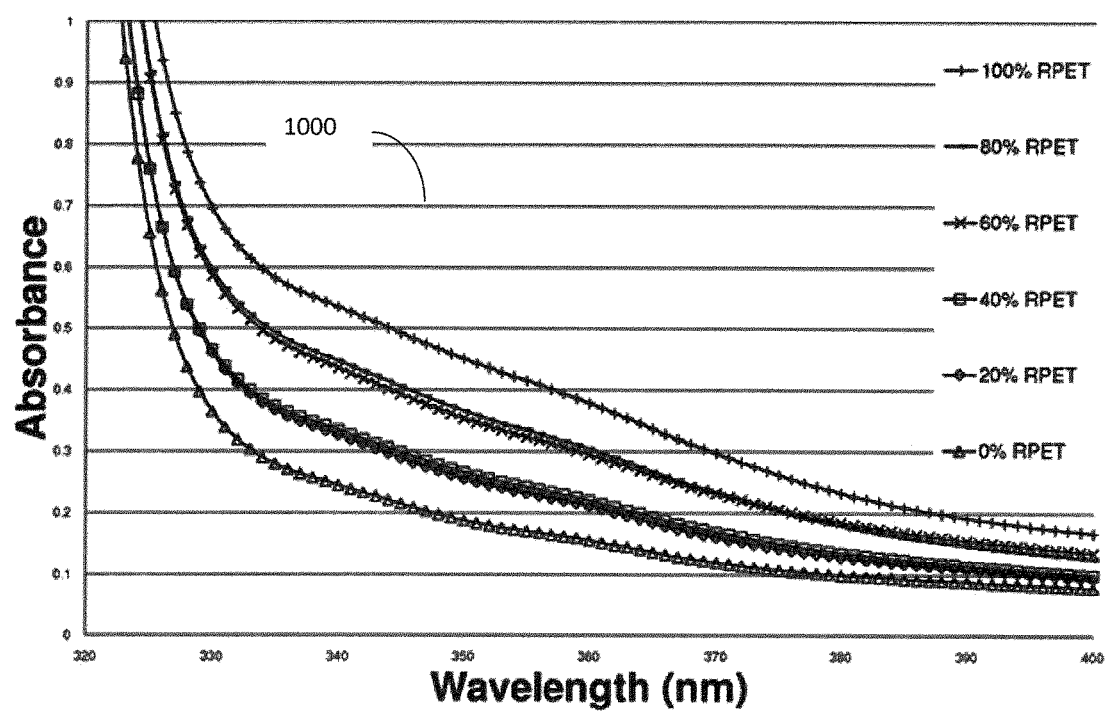
FIG. 10 is an absorbance graph reporting patterns of percentages of post-consumer recycled thermoplastics in accordance with one variation of the embodiment of FIG. 6.

Referring to FIGS. 9 & 10 a schematic diagram and an absorbance graph are shown in accordance with one variation of the embodiment of FIG. 6. Described in general terms, the current embodiment of the invention employs methods to verify the percentage of post-consumer recycled to virgin thermoplastic content (PCR); the brain 601, and decision point 119. In the present example embodiment of this invention, optical detection of the percentage of post-consumer recycled to virgin polyethylene terephthalate thermoplastic (% PCR) is made using ultraviolet-visible spectroscopy, UV-Vis, 900. In this embodiment, the brain 601 controls the light source via optical fiber for light flash 907. The light flash is sent to the collimator lens 906; through extruded thermoplastic material within cover plates 905; then to the aperture 904; through the second collimator lens 902; to the optical fiber detector 902. The stereomicroscope 908 captures the light which is sent to the UV-Vis spectrometer 909 and refractometer 910 and then to decision point 119 via the brain 601 for analysis. In other embodiments of system 900, UV-Vis spectroscopy may be done using a SSEF Instruments UV-VIS portable spectrometer or an Ocean Optics USB2000-UV-VIS Miniature 30. Fiber Optic Spectrometer. The ultraviolet-visible spectroscopy 900 measures the intensity of light passing through a sample, I, and compares it to the intensity of light before it passes through the sample, $I_o$. The ratio of I to $I_o$ is the transmittance, and is usually expressed as a percentage, % T. The absorbance, A, is based on the transmittance is given as A=−log(% T/100%). UV-Vis spectroscopy yields absorbance curves that reflect % PCR, the percentage of post-consumer recycled to virgin thermoplastic material. In the absorbance curves example in FIG. 10, the absorbance curves are presented as 1000 of FIG. 10 for various percentages of recycled polyethylene terephthalate, (% RPET). UV-Visible spectroscopy was used to detect the light transmission of the six types of PET sheets. The UV-visible analyses were performed using a Perkin-Elmer Lambda 25 system (Waltham, Mass., USA) with an integrating reflectance spectroscopy accessory (model RSA-E-20, Labsphere®, North Sulton, N.H., USA); measurements were carried out at 480 nm/min and a wavelength range of 190-800 nm in transmittance (%) mode. The curves in FIG. 10 are presented as absorbance. At least five samples of each PET type were scanned.

In general, indicators of % PCR such as absorbance may be mapped to % PCR by any transformation that maps probabilities into the real given that the transformation is one-to-one, continuous and differentiable. In general terms, suppose g(•) is a cumulative distribution function of a random variable on the real line and express % PCR as the blend probability corresponding to % PCR, as $\pi_i = g(\eta_i)$, where $-\infty < \eta_i < +\infty$. As such, one could use the generalized linear modeling inverse transformation, $\eta_i = g^{-1}(\pi_i)$, as the link function where for $0 < \pi_i < 1$, McCullagh, P. and J. A. Nelder (1989), Generalized Linear Models, Second Edition, Chapman & Hall/CRC Monographs on Statistics and Applied Probability, ISBN-13: 978-0412317606.

Other embodiments may be used to verify the target level of % RPET include but are not restricted to multinomial logit and probit models, additive logistic normal distribution, censored normal distributions (tobit), normal distribution with nonlinear response function, beta distribution regression, simplex distribution regression, and quasi-parametric regression. Moreover, the mapping of indicator variables onto discrete categories of % RPET may also be obtained by numerical methods such as but not restricted to artificial neural network analysis.

The absorbance curves data 1000 for the corresponding target % PCR define a % PCR pattern signature, 1203 of system 1200.

The system and method 900 may include but is not restricted to the physical, mechanical, thermal, and optical properties of thermoplastics presented in "Systems and Methods for Determining Recycled Thermoplastic Content", U.S. Pat. No. 8,063,374 B, Date of Patent: Nov. 22, 2011 and by Curtzwiler, G., K. Vorst, J. E. Danes, R. Auras, and J. Singh (2011) and Kang, D. H., R. Auras, K. Vorst, and J. Singh (2011). Other embodiments of this invention may use multiple sensors of % PCR and thus make use of both supervised and unsupervised neural network models.

Figure 12:
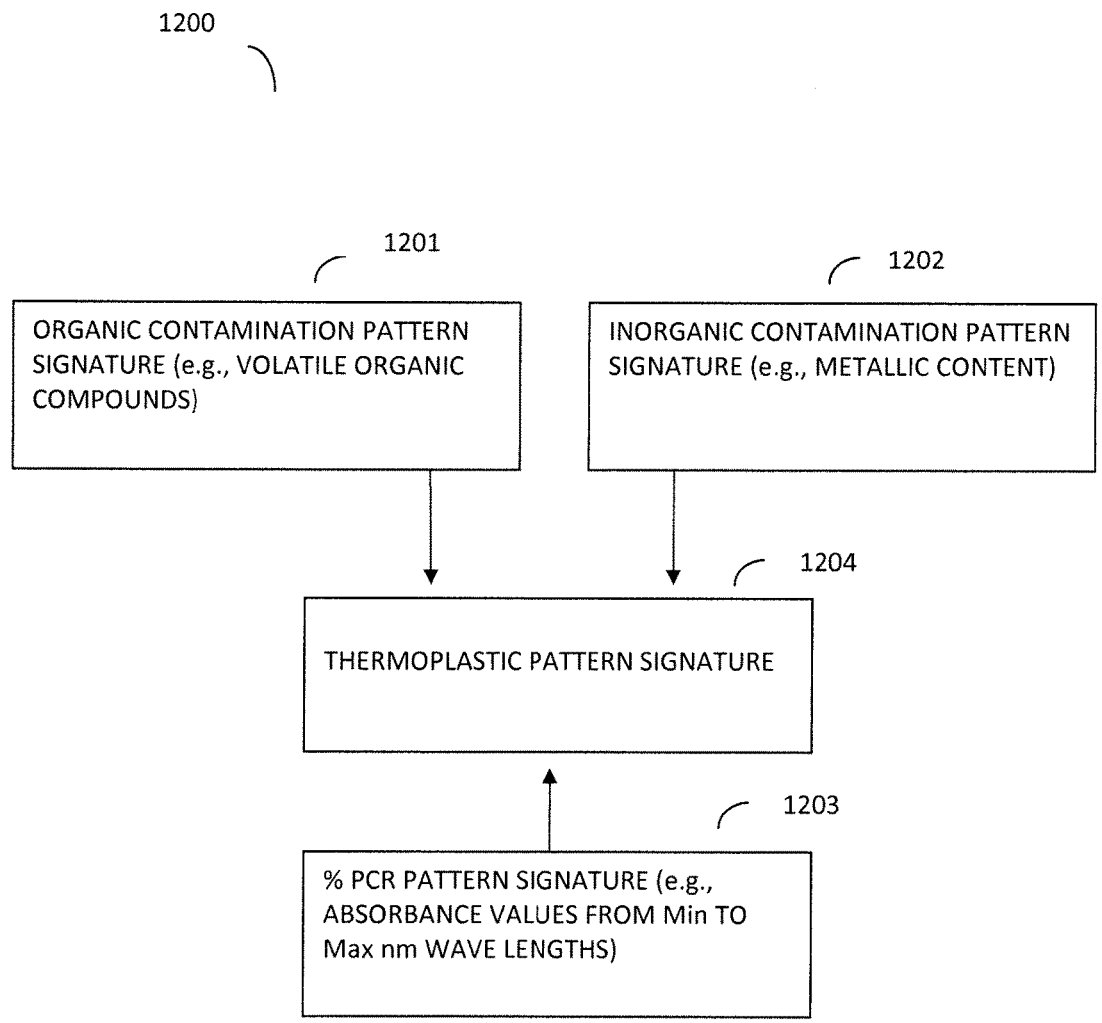
FIG. 12 is a block diagram of a system for comprising a thermoplastic pattern signature in accordance with alternate variations of the embodiments of FIG. 6.

Referring to FIG. 12, shown is a block diagram in accordance with one variation of the embodiment of FIG. 6. The present embodiment employs but is not restricted to three pattern signatures: an organic contamination pattern signature 1201, an inorganic contamination pattern signature 1202, and a % PCR pattern signature 1203. The organic contamination pattern signature 1201 is the sensors' sensitivity to various contaminants, the probabilities of prediction, and the actual predicted contaminants. The inorganic contamination pattern signature 1202 is the ppm for of each of the n elements. The % PCR pattern signature 1203 is the absorbance curves data in 1000 for the corresponding target % PCR. Collectively, these three pattern signatures create a statistically unique thermoplastic pattern signature 1204. However, other embodiments of this invention may define these pattern signatures and various other pattern signatures in different ways using but not restricted other variables and measurements. Additionally, thermoplastic properties unrelated to organic and inorganic contamination or % PCR may be used to create thermoplastic pattern signatures.

Figure 13:
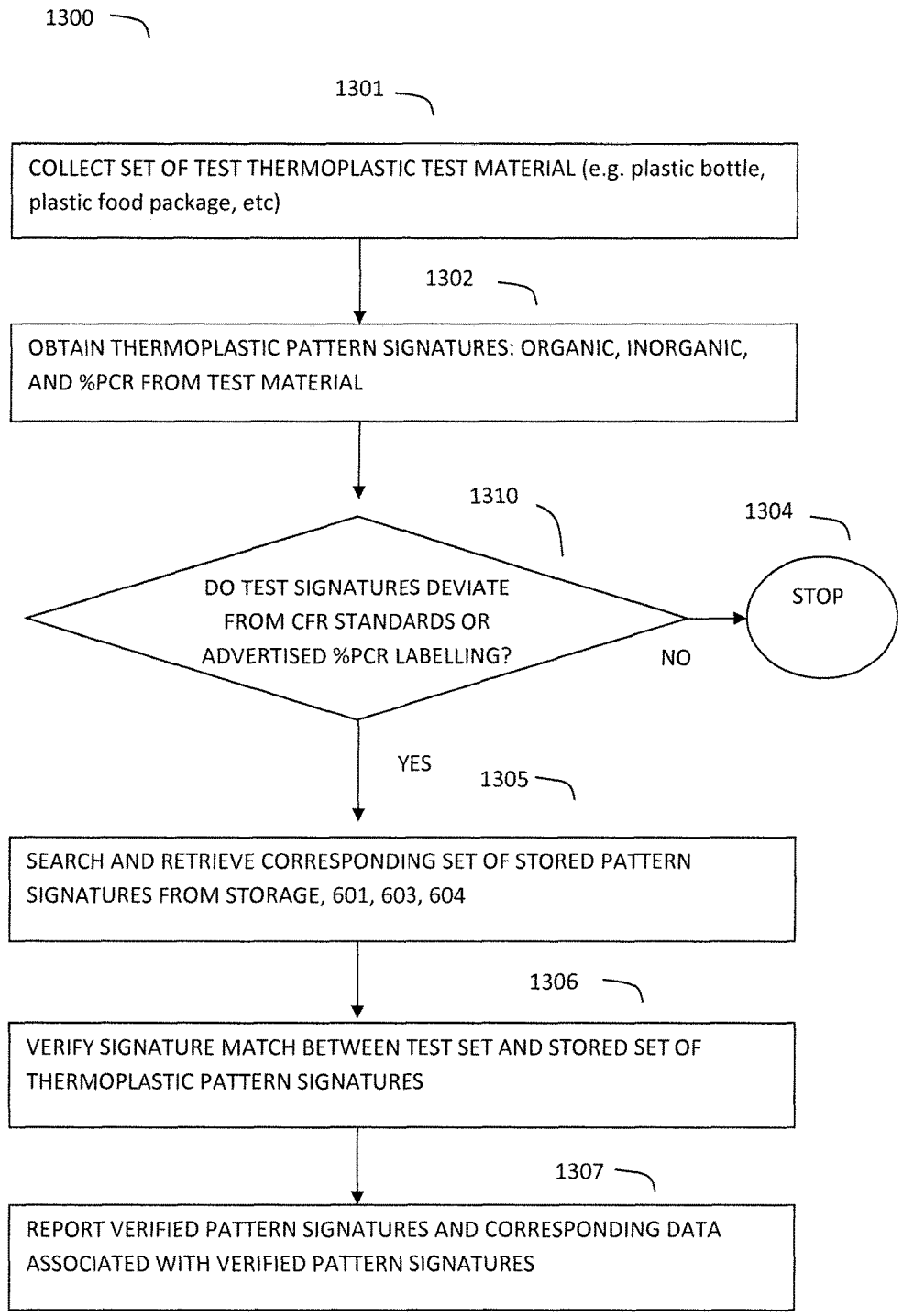
FIG. 13 is a flow chart illustrating a method of empirically testing and verifying safety claims and advertised % PCR claims in accordance with one variation of the embodiment of FIG. 1.

Referring to FIG. 13, shown is a flow chart illustrating a method in accordance with one variation of the embodiment of FIG. 1. The method provides one example of matching a test set of thermoplastic pattern signatures 1302 with the corresponding set of thermoplastic pattern signatures 1204 stored in the conversion line brain 601 or the plant server 603 or the plant complex server 604. Suppose a manufacturer has faithfully implemented system 100 for its thermoplastic conversion lines. Further suppose, for example, one desires to challenge the advertised % PCR and safety claims made by the manufacturer and selects a sample of thermoplastic food packaging from a retail outlet. In this example embodiment, batch testing is required to obtain the test pattern signatures 1302. The unknown thermoplastic material 1301 to be evaluated is processed by measurements (e.g., 700, 800, and 900) or equivalents. The resulting test thermoplastic pattern signatures obtained 1302 are tested 1310 for deviations from CFR standards and advertised % PCR claims. If no deviations from the advertised % PCR and safety claims are found the process stops, 1304. If the deviations are found then the measurements from 1302 which define the test signatures need to be verified 1306. A search/retrieval of the corresponding set of stored thermoplastic pattern signatures 1305 is done by searching the database in the brain 601 or the plant server 603 or the plant complex server 604 and retrieves a matching signature.

In alternate embodiments of this invention, the test for deviation 1310 is skipped so as to validate the assumption that the test product was indeed manufactured by the assumed manufacturer. In a conversion line only embodiment, the search and retrieval is done via the brain 601. In the single plant embodiment, the search and retrieval is done via the plant server 603. In the multiple plant (plant complex) embodiments, the search and retrieval is done via the plant complex server 604.

Search is obtained by search algorithms defined by not restricted to those presented by Edelkamp, S. (2011), Heuristic Search Theory and Applications, Morgan Kaufmann, ISBN-13: 978-0123725127.

Verification of the match between signatures 1306 is quantified by matching metrics such as but not restricted to Euclidean distance, Euclidean distance squared, Manhattan (city-block) distance, Pearson correlation coefficient; Pearson squared correlation, Chebychev Distance, Spearman correlation, mean squared error, root mean squared error, mutual information, Kullback-Leibler divergence (relative entropy), and symmetric versions of Kullback-Leibler divergence.

In the current embodiment of this invention, documentation of the matched thermoplastic signatures 1307 is provided digitally and by a paper report of the two matching thermoplastic patters signatures 1306 and associated manufacturing characteristic data 104.

While the invention herein disclosed has been described by means of specific embodiments, examples and applications thereof, numerous modifications and variations could be made thereto by those skilled in the art without departing from the scope of the invention set forth in the claims.

What is claimed is:

1. A method comprising:
  providing a thermoplastic test material;
  providing at least one sensor;
  detecting a plurality of parameters in the thermoplastic test material using the at least one sensor;
  generating a plurality of outputs in response to the detecting;
  providing at least one thermoplastic pattern signature, each thermoplastic pattern signature tied to manufacturing data taken during manufacturing of a thermoplastic material, wherein said manufacturing data includes a measurement of contamination and identification of a manufacturer physical plant; and
  validating, automatically, the thermoplastic test material as a function of the plurality of outputs having been generated and the thermoplastic pattern signature, wherein the validating includes verifying a match between the plurality of outputs having been generated and the thermoplastic pattern signature;

generating a report of the validating of the thermoplastic test material, including the validating that the thermoplastic test material was manufactured by the manufacturer physical plant.

2. The method of claim 1 further comprising
converting the thermoplastic test material wherein the converting consists of at least one process selected from a group of processes consisting of injection molding, compression molding, transfer molding, rotational molding, extrusion, blow molding, blown film extrusion, thermoforming, calendaring, fibering, foaming, and laminating.

3. The method of claim 1 further comprising storing the thermoplastic pattern signature.

4. The method of claim 3 wherein the storing comprises digitally storing the plurality of outputs on at least one of a conversion line, a plant server, and a plant complex server.

5. The method of claim 1 further comprising retrieving the thermoplastic pattern signature from storage including digitally retrieving the thermoplastic pattern signature from at least one of a conversion line storage, a plant storage, and/or a plant complex storage.

6. A method comprising:
providing a thermoplastic test material;
providing at least one sensor;
detecting a plurality of parameters in the thermoplastic test material using the at least one sensor;
generating a plurality of outputs in response to the detecting;
providing at least one thermoplastic pattern signature, each thermoplastic pattern signature tied to manufacturing data taken during manufacturing of a thermoplastic material, wherein said manufacturing data includes a measurement of contamination and identification of a manufacturer physical plant; and
validating, automatically, a percentage of post-consumer recycled thermoplastic content in the thermoplastic test material as a function of the plurality of outputs having been generated and the thermoplastic pattern signature, wherein the validating includes verifying a match between the plurality of outputs having been generated and the thermoplastic pattern signature;
generating a report of the validating of the thermoplastic test material, including the validating that the thermoplastic test material was manufactured by the manufacturer physical plant.

7. The method of claim 6, further comprising
converting the thermoplastic test material wherein the converting consists of at least one process selected from a group of processes consisting of injection molding, compression molding, transfer molding, rotational molding, extrusion, blow molding, blown film extrusion, thermoforming, calendaring, fibering, foaming, and laminating.

8. The method of claim 6, wherein the thermoplastic test material is a blend comprising the ratio of recycled thermoplastic material to virgin thermoplastic material.

9. The method of claim 6, wherein the detecting comprises using the at least one sensor to detect patterns that reflect different percentages of post-consumer recycled thermoplastic content.

10. The method of claim 6, further comprising storing the thermoplastic pattern signature.

11. The method of claim 10 wherein the storing comprises digitally storing the plurality of outputs on a at least one of a conversion line, a plant server, and a plant complex server.

12. The method of claim 6, retrieving the thermoplastic pattern signature from storage including of digitally retrieving the thermoplastic pattern signature from at least one of a conversion line storage, a plant storage, and/or a plant complex storage.

13. A method comprising:
providing a thermoplastic test material;
detecting a first plurality of parameters in the thermoplastic test material using at least one sensor;
storing a set of thermoplastic pattern signatures in response to the detecting of the first plurality of parameters in the thermoplastic test material, wherein each of the set of thermoplastic pattern signatures are tied to manufacturing data taken during manufacturing of a thermoplastic material, wherein said manufacturing data includes a measurement of contamination and identification of a manufacturer physical plant;
detecting a second plurality of parameters in the thermoplastic test material using the at least one sensor;
validating, automatically, the thermoplastic test material as a function of the detecting of the second plurality of parameters in the thermoplastic test material and the set of thermoplastic pattern signatures having been stored, wherein the validating includes verifying a match between the second plurality of parameters having been detected and the set of thermoplastic pattern signatures having been stored; and
generating a report of the validating of the thermoplastic test material, including the validating that the thermoplastic test material was manufactured by the manufacturer physical plant.

14. The method of claim 13, wherein the verifying comprises computing a search algorithm that compares an equivalence of the thermoplastic pattern signatures comprising a test set of thermoplastic pattern signatures with the set of thermoplastic pattern signatures having been stored.

15. The method of claim 14 wherein the verifying comprises determining a statistical metric that quantifies a correspondence of a thermoplastic pattern signatures in the test set and a thermoplastic pattern signature in the set having been stored.

* * * * *